United States Patent [19]

Clark

[11] 4,336,809
[45] Jun. 29, 1982

[54] HUMAN AND ANIMAL TISSUE PHOTORADIATION SYSTEM AND METHOD

[75] Inventor: William G. Clark, Pittsford, N.Y.

[73] Assignee: Burleigh Instruments, Inc., Fishers, N.Y.

[21] Appl. No.: 131,022

[22] Filed: Mar. 17, 1980

[51] Int. Cl.$^3$ ............................................. A61B 6/00
[52] U.S. Cl. ................................. 128/665; 128/303.1; 128/398
[58] Field of Search ............. 128/303.1, 395, 632–634, 128/630, 635, 664, 665, 6, 7, 23, 397, 398, 207.21, 207.22; 200/61.52, 61.47, 63.30; 219/121 L, 121 LM, 121 LB, 121 LT, 121 LA, 121 LP

[56] References Cited

U.S. PATENT DOCUMENTS

| | | | |
|---|---|---|---|
| 1,791,794 | 2/1931 | Chesney | 128/398 |
| 2,056,990 | 10/1936 | Symonds | 128/398 |
| 3,417,745 | 12/1968 | Sheldon | 128/6 |
| 3,750,670 | 8/1973 | Palanos et al. | 128/303.1 |
| 3,769,963 | 11/1973 | Goldman et al. | 128/303.1 |
| 3,821,510 | 6/1974 | Muncheryan | 128/207.22 |
| 3,834,391 | 9/1974 | Block | 128/303.1 |
| 3,843,865 | 10/1974 | Nath | 128/395 |
| 3,936,631 | 2/1976 | Muska | 250/227 |
| 4,043,033 | 8/1977 | Yeo | 200/61.52 |
| 4,072,147 | 2/1978 | Hett | 128/6 |
| 4,120,293 | 10/1978 | Muckerheide | 128/395 |
| 4,161,944 | 7/1979 | Muckerheide | 128/654 |
| 4,170,997 | 10/1979 | Pinnow et al. | 128/303.1 |
| 4,207,874 | 6/1980 | Choy | 128/303.1 |
| 4,266,548 | 5/1981 | Davi | 128/303.1 |
| 4,266,549 | 5/1981 | Kimura | 128/303.1 |

FOREIGN PATENT DOCUMENTS

| | | | |
|---|---|---|---|
| 2542590 | 4/1977 | Fed. Rep. of Germany | 350/96.10 |
| 2647618 | 4/1978 | Fed. Rep. of Germany | 219/121 L |

OTHER PUBLICATIONS

Dougherty, T. J.; *Photoradiation Therapy for the Treatment of Malignant Tumors*, in Cancer Research, vol. 38, pp. 2628–2635, 8/78.

Doiron, D. R.; *Fluorescence Bronchoscopy for Detection of Lung Cancer;* in Chest, 76; Jul. 1, 1979.

*Primary Examiner*—Lee S. Cohen
*Attorney, Agent, or Firm*—Martin Lukacher

[57] ABSTRACT

A tissue photoradiation system uses a hematoporphyrin or hematoporphyrin derivative dye in tissue to be irradiated and arranges a xenon ion laser 10 for simultaneous lasing. Deep blue light is produced at wavelengths of about 406–427 nanometers and red light at a wavelength of about 627 nanometers by using partially transmitting mirrors 12 and 13 arranged at opposite ends of the laser resonator. Mirror 12 has a coating 14 that substantially reflects blue light and partially transmits red light to produce a red light output, and the coating 15 of mirror 13 substantially reflects red light and partially transmits blue light producing a blue light output. The blue light output is transmitted to a diagnostic tissue irradiator 21 to illuminate the tissue and diagnose its condition. A transmission system using an optical fiber 25 delivers the red light to the tissue for treatment purposes. The red light is radiated out the side of an optical fiber region 30a to be directed into large area of tissue.

13 Claims, 5 Drawing Figures

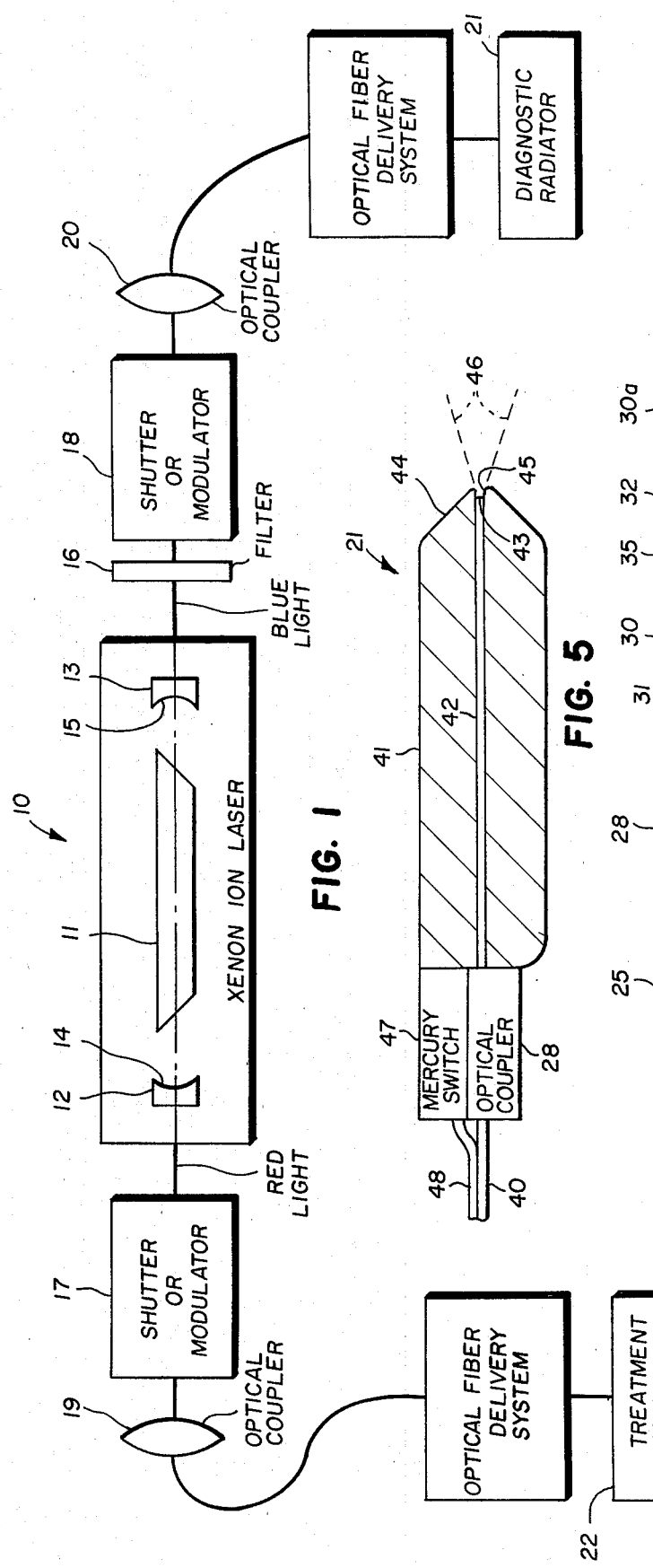

HUMAN AND ANIMAL TISSUE PHOTORADIATION SYSTEM AND METHOD

BACKGROUND

Medical workers have discovered that certain dyes not only selectively stain neoplastic or tumorous tissue but also fluoresce in response to irradiation and are photodynamically cytotoxic in response to a proper wavelength of light in the presence of oxygen within living tissue. One of the dyes that is presently preferred for these characteristics contains hematoporphyrin or hematoporphyrin derivatives that when administered intravenously remain at higher concentrations for longer periods of time in traumatized or malignant tumorous tissue than in normal tissue. This dye also has a strong absorption peak centered at a wavelength of approximately 407 nanometers and responds to excitation at about this wavelength by fluorescing at a wavelength of about 614 nanometers. This makes tumor diagnosis possible by injecting the dye, allowing it to concentrate in tumorous tissue, irradiating the tissue with deep blue violet light, and observing red fluorescence. This same dye has a photodynamic absorption peak at a wavelength of about 631 nanometers and is cytotoxic to malignant tissue containing the dye when irradiated with red light of about this wavelength.

For diagnostic purposes, present workers have been using the krypton ion laser for its 406.7/413.1 nanometer lines matching the 407 nanometer absorption peak of hematoporphyrin. For treatment purposes, they have used several light sources including a xenon arc lamp filtered to transmit only red light, a Helium-Neon laser operating at 632.8 nanometers, and an argon ion laser-pumped Rhodamine-B dye laser tuned to about 631 nanometers.

My invention recognizes the problems involved in this art and suggests a way that a single laser can simultaneously provide both frequencies required for diagnosis and treatment. I also suggest practical ways of transmitting the light to the tissue and more convenient and economical equipment for medically practicing photoradiation diagnosis and treatment.

SUMMARY OF THE INVENTION

My invention comprises a tissue photoradiation system using a hematoporphyrin or hematoporphyrin derivative dye in the tissue to be irradiated. A xenon ion laser arranged for simultaneous lasing produces deep blue diagnostic light at wavelengths of about 406-427 nanometers and red treatment light at a wavelength of about 627 nanometers, and partially transmitting mirrors arranged at opposite ends of the resonator of the laser help accomplish this. A coating on one of the mirrors substantially reflects blue light and partially transmits red light producing a red light output, and a coating on the other mirror substantially reflects red light and partially transmits blue light to produce a blue light output. The blue and red light are transmitted to the tissue respectively for diagnosis and treatment purposes, and my invention includes equipment to facilitate this.

DRAWINGS

FIG. 1 is a schematic view of a preferred embodiment of a light source and delivery system according to my invention;

FIG. 2 is a schematic view of an optical fiber delivery system for treatment according to my invention;

FIG. 3 is a schematic, cross-sectional view of a preferred embodiment of optical needle for treatment according to my invention;

FIG. 4 is a fragmentary, schematic cross-sectional view of the needle of FIG. 3 embedded within a tumor for treatment; and FIG. 5 is a partially schematic, cross-sectional view of a manipulable illuminator usable for diagnosis or treatment according to the invention.

DETAILED DESCRIPTION

For tissue photoradiation with hematoporphyrin dyes, I prefer a xenon ion laser, which is generally known. Xenon ion lasers have a singly ionized lasing transition in the red range at a wavelength of about 627 nanometers nearly matching the red absorption peak of hematoporphyrin; and they also have a group of doubly ionized lines at wavelengths of about 406, 421, 424, and 427 nanometers, one or more of which can match the 407 nanometer blue absorption peak of hematoporphyrin. A single xenon ion laser providing both deep blue light for diagnostic use and red light for treatment saves considerably in requiring only a single light source to be bought and serviced. Moreover, the fact that the red and blue lasing transitions of a xenon ion laser result from single and double ionized states of the gain medium indicates that these frequencies are non-competitive and can be made to lase simultaneously. This makes both effective frequencies available at any time for convenient and rapid changing between diagnosis and treatment modes.

To produce both the desired red and blue lights from a single xenon ion laser at the same time, I prefer partially reflecting and transmitting mirrors 12 and 13 at opposite ends of a resonator for laser 10. Mirror 12 has a coating 14 that reflects deep blue and partially transmits red to produce a red light output, and mirror 13 has a coating 15 that reflects red and partially transmits blue to produce a blue light output. Coatings 14 and 15 for mirrors 12 and 13 are within the skill of optical coating designers to produce the suggested result. The coatings and mirrors then effectively output red and blue light from opposite ends of laser 10 simultaneously, because these frequencies occur non-competitively from different ionized states that can coexist within plasma tube 11.

The rest of the problem is to transmit the red and blue light to the tissue in ways that are satisfactory to achieve medical diagnosis and treatment. Although many alternatives are possible, the following are presently preferred.

The blue light available from laser 10 is used primarily for diagnostic purposes but is also somewhat photodynamic and has a cytotoxic effect under some circumstances. The main use of the blue light is to illuminate tissue and observe the fluorescence effect from the tissue containing hematoporphyrin to identify tumors and other traumatized tissue. Since any red light mixed in with the blue would tend to mask the red fluorescence, filter 16 insures that no coherent or incoherent red radiation from laser 10 passes through the transmission system for the blue light. The single wavelength of red light out of the other end of laser 10 is used primarily for treatment by producing cytotoxic effects and needs no filtering. Shutters 18 can block or pass the desired light, and modulators 17 can regulate the intensity of transmitted light. The intensity of light from the laser source can also be regulated by modulating plasma tube current density. Optical couplers 19 and 20 transmit red and blue light respectively to optical fiber transmission systems leading to the tissue.

Laser 10 can be in or near an operating room and transmit red and blue light via couplers and optical fiber systems to the operating theater. There, the blue light is preferably delivered via a diagnostic illuminator or radiator 21, providing a small and manipulable instrument for irradiating exposed tissue surfaces to observe any fluorescence from dye retained within the tissue. Goggles that transmit only red light can enhance the fluorescence signal, and blue light is sufficiently photodynamic in some circumstances to kill thin surface tissues so that treatment can be involved in using blue light. An endoscope of the type described in U.S. Pat. No. 4,072,147 can also deliver blue diagnostic light or red therapeutic light into a body cavity. A treatment radiator 22 is also available for radiating red light into tissue to be killed, and my invention includes preferred embodiments of a diagnostic illuminator 21 and a treatment radiator 22.

Illuminator 21 as shown in FIG. 5 is preferably the size of a penlight so that it is easily manipulated to illuminate tissue and observe fluorescence from tissue containing hematoporphyrin. An optical coupler 28 couples illuminator 21 to an optical fiber 40 delivering blue light; and illuminator 21 is preferably formed as a small, knurled cylinder 41. An optical fiber 42 leads through cylinder 41 and terminates at a forward end 43 in a recess 45 at the forward end 44 of cylinder 41 where the recessed fiber 42 is protected and its end 43 is kept clean and operable. Recess 45 helps define the angle of light cone 46 from fiber 42, and the cone angle 46 can also be established by a lens or other optical element on the terminal end 43 of fiber 42.

With such an arrangement, fiber 42 delivers blue light at a suitable radiation angle for illuminating tissue to observe fluorescence from the presence of hematoporphyrin in tumors or traumatized tissue for diagnostic purposes. The small size and manipulable ease of illuminator 21 makes this possible under many different medical circumstances. The mechanisms of energy transfer that produce the fluorescence can also have a cytotoxic effect so that the very act of detecting small, thin placques such as found in a lung, for example, can destroy the tumors with the blue light normally used for diagnostic purposes. It is also possible to mount illuminator 21 in place to irradiate and destroy surface tumors, thus serving as a treatment, rather than as a diagnostic, tool. Moreover, illuminator 21 can use radiant energy from sources other than xenon ion laser 10.

Mercury switch 47 schematically shown at the rear end of cylinder 41 can also be located elsewhere within cylinder 41 and be electrically connected to shutter 18 by line 48 accompanying optical fiber 40. Switch 47 is preferably oriented so that light cone 46 must be aimed below the horizontal to reduce the hazard of accidentally directing blue light into the eyes of workers in the vicinity of illuminator 21.

Considerable radiation must be transmitted to kill large tumor masses by photoradiation; and the required radiation can cause overheating, especially if it is concentrated in too small a region. This causes problems in delivering radiant energy out of the end of an optical fiber, making a small hot spot that burns the adjacent tissue making it opaque to radiation. Thermal sources such as xenon arc lamps also pose difficulties in transmitting adequate radiation to deep seated tumors, because extended sources cannot be coupled efficiently to optical fibers. Problems of distributing radiation throughout the region of a tumor to be killed are also formidable.

My invention makes an optical fiber delivery system into a linear light radiator that radiates light out the side of an optical fiber for spreading the radiation over a wider area and delivering it more effectively to a tumor. Some of my preferences for accomplishing this are schematically illustrated in FIGS. 2–4.

An optical fiber 25 can have a side radiating end region 26 embedded in a tumor 27 as schematically illustrated in FIG. 2 to form a linear radiator dispersing light widely within the tumor and speeding up and simplifying cytotoxic treatment. There are several ways that end region 26 of optical fiber 25 can be formed as a linear side radiator. A preferred way of doing this is to form optical needles as schematically illustrated in FIGS. 3 and 4.

An optical needle serving as a linear radiator can be coupled to an optical fiber 25 by a conventional optical coupler 28. The needle includes a fiber optic core 30 that is generally internally reflecting. Core 30 is surrounded by a cladding 31 as generally known; but in an end region 30a, a different cladding 32 surrounds the core to make it into a radiator, instead of an internally reflecting transmitter. Optical needles can also be made disposable in different lengths for implanting to different depths in tissue, and such optical needles can radiate light out the side of optical fiber 30 for their entire length.

There are several ways that side radiation of energy from an optical fiber core 30 can be accomplished. One way is to chose a ratio of the indexes of refraction between cladding 32 and core end region 30a so that internal reflection within core region 30a is substantially less than total. This causes light to radiate outward through the side of core region 30a and through preferably transparent cladding 32.

Another way is to alter the interface between core 30a and cladding 32 to increase side radiation. Giving the surface of core region 30a a ground glass effect is one possibility; another is positioning or embedding light-scattering elements such as tiny particles at the surface of core 30a near the interface with cladding 32. Light-scattering particles can also be embedded throughout cladding 32 to enhance the side delivery of radiation. Combinations of these measures are also possible. A reflective coating 33 covering the free end of core region 30a can prevent light from escaping from the free end of the core and reflect light back along the core for radiation from the side of core 30 through cladding 32. An end cap 34 having a beveled end can be placed on the forward end of the optical needle as shown in FIGS. 3 and 4 to facilitate its insertion into tissue, and many mechanical and structural possibilities are available to optical needles having the right characteristics to radiate light out of the sides of their core fibers.

An optical needle for linearly irradiating tissue can also include a retractable metal sleeve 35 surrounding cladding 32 for added strength during implantation. Sleeve 35 can be a conventional needle that penetrates tumor tissue to be irradiated and then retracts to the tumor surface as shown in FIG. 4 to leave the clad fiber embedded in the tumor for treatment. Transparent cladding 32 can be formed of a clear and tough resinous material to offer mechanical strength and security to core region 30a so that core and cladding can be safely implanted within a tumor 36 as shown in FIG. 4 and disperse treatment light throughout a wide region of the tumor.

Instead of a protective metal sleeve, cladding material 32 can be made stronger with a larger diameter than usually required for optical fibers to provide the strength necessary for safely implanting the optical needle in a tumor. Optical needles with strong cladding 32 can be made in different lengths to accommodate different sizes and depths of tumors to be treated.

A preferred optical needle according to my invention would be made simply and cheaply enough to be disposable after each use. Many different configurations in sleeves, claddings, and dimensions are possible, with optimum choices being controlled by economics, convenience, and effectiveness.

I claim:

1. A tissue photoradiation system using a hematoporphyrin or hematoporphyrin derivative dye in tissue to be irradiated, said system comprising:
   a. a xenon ion laser arranged for simultaneous lasing to produce deep blue light at wavelengths from about 406 to 427 nanometers and red light at a wavelength of about 627 nanometers;
   b. partially transmitting mirrors arranged at opposite ends of a resonator for said laser;
   c. one of said mirrors having a coating that substantially reflects said blue light and partially transmits said red light to produce a red light output;
   d. the other of said mirrors having a coating that substantially reflects said red light and partially transmits said blue light to produce a blue light output;
   e. means for transmitting said blue light output to said tissue to diagnose the condition of said tissue; and
   f. means for transmitting said red light output to said tissue for treatment purposes.

2. The photoradiation system of claim 1 wherein said blue light transmitting means includes an optical fiber, a manipulable illuminator, and means for radiating said blue light from an end of said optical fiber terminating in said illuminator.

3. The photoradiation system of claim 2 wherein said illuminator includes mercury switch means arranged to permit said blue light to be directed only below the horizontal.

4. The photoradiation system of claim 1 wherein said means for transmitting said red light includes an optical needle having an optical fiber core and a transparent cladding around said core.

5. The photoradiation system of claim 4 wherein said fiber and said cladding have a ratio of indexes of refraction so that internal reflection within said fiber is substantially less than total.

6. The photoradiation system of claim 4 wherein light scatterers are arranged in the region of the interface between said fiber core and said cladding.

7. The photoradiation system of claim 4 wherein light scatterers are embedded in said cladding.

8. The photoradiation system of claim 4 wherein said optical fiber core has opposite ends into one of which said output red light is injected and the other of which is a free end including a reflective surface formed on the free end of said optical fiber core.

9. The photoradiation system of claim 4 including a retractable, protective sleeve around said cladding of said optical needle.

10. The method of photoradiation therapy which comprises simultaneously generating with a single laser radiation of at least two different wavelengths which excite malignant cells when a photosensitizer is present therein to cause flurorescence from at least one of said wavelengths and cytotoxic effects from at least another of said wavelengths therein, and delivering said radiation of each of said wavelengths to irradiate said cells.

11. The invention as set forth in claim 10 wherein said delivering step is carried out selectively for each of said wavelengths.

12. The invention as set forth in claim 11 wherein said delivering step is carried out by introducing an optical fiber which carries at least said cytotoxic wavelength into a tissue mass containing said cells, and projecting said cytotoxic wavelength from the side periphery of said fiber into said mass.

13. The invention as set forth in claim 11 wherein said delivering step is carried out by projecting a beam of said radiation, and changing the direction of said beam manually to be incident upon tissue containing said cells.

* * * * *